United States Patent [19]

Telchin

[11] Patent Number: 4,953,970
[45] Date of Patent: Sep. 4, 1990

[54] SELF EXAMINATION DEVICE

[76] Inventor: Arthur Telchin, 160 E. 48th St., New York, N.Y. 10028

[21] Appl. No.: 352,066

[22] Filed: May 15, 1989

[51] Int. Cl.⁵ .............................................. A61B 3/02
[52] U.S. Cl. .................................... 351/223; 350/621
[58] Field of Search ............... 351/223, 247; 132/301, 132/316; 362/135, 136; 350/621

[56] References Cited

U.S. PATENT DOCUMENTS

| 2,026,009 | 3/1933 | Ritz-Woller . | |
|---|---|---|---|
| 2,026,010 | 3/1933 | Ritz-Woller . | |
| 2,135,743 | 3/1936 | Cassity . | |
| 2,582,227 | 12/1948 | Brady . | |
| 3,751,140 | 8/1973 | Berlin et al. | 350/621 |
| 4,120,563 | 10/1978 | Stefanou . | |
| 4,750,831 | 6/1988 | Vega . | |

Primary Examiner—Paul M. Dzierzynski
Attorney, Agent, or Firm—Stanley J. Yavner

[57] ABSTRACT

An eye self-examination device is provided with an objective lens mounted over a mirror into which the patient looks for the purposes of detecting foreign or unwanted matter within or around the eye. A light source having an appropriate power source is provided proximate the lens and mirror in order to illuminate the eye. The device can be used in a hand-held orientation or is provided with mounting means, such as legs on the housing, for positioning the device on a table. Furthermore, a storage compartment for swabs or other items related to cleaning the eye is provided within the housing.

9 Claims, 2 Drawing Sheets

SELF EXAMINATION DEVICE

BACKGROUND OF THE INVENTION:

Typically, it has been the practice to examine one's own eye by the use of a mirror. However, the use of an ordinary mirror for this purpose is not suitable because magnification is required to analyze problems such as dirt particles or contact lens problems, or the like. Even if one uses magnification in the mirror, there are still the problems relating to proper illumination of the eye, portability, as well as providing a readily available facility for curing the dirt or contact lens problem immediately after detection.

In the prior art, inventors such as Vega in patent No. 4,750,831, issued June 14, 1988, have provided a self-examination apparatus with a concave lens supported in a housing. Illumination is provided by an incandescent light source back lighting the lens, which is supported within a highly reflective chamber of the housing. Drawbacks to systems such as Vega relate to the inadequate illumination provided by the light source mounted beneath the lens, the inability to adjust the direction or intensity of the light source and the lack of consideration given to tailoring the focusing characteristics of the device to the visual needs of the user. Furthermore, once the problems are identified using the self examination device, there should be a means for curing the problem readily at hand, such as an instrument, medicine or a cleaning implement. Still further, the self examination device should provide a means for freeing the user's hands to cure the problem after its discovery. Generally, the prior art has not addressed the foregoing drawbacks.

Accordingly, a primary object of the present invention is to provide a self examination device for the eye which is portable, has adequate illumination, provides the convenience of cleaning implements in a handy receptacle, accommodates for hands-free treatment to cure problems and adapts to particular lighting, magnification and focussing requirements.

A further and more particular object of the present invention is to provide a self examination device which may either be used in a portable manner or in a permanently connected manner, insofar as a power supply for illumination is concerned.

A still further object of the present invention is to provide, in connection with a self examination device for the eye, a light source that can be directed or focussed for the particular circumstance of use.

As a still further object of the present invention, a self examination device for the eye is provided with a light source with adjustable intensity utilizing either standard incandescent means or fiber optic devices for illumination.

A final stated object of the present invention is to enable optical means of a self examination device for the eye to be protected from damage when not in use and further means for facilitating cleaning thereof.

BRIEF DESCRIPTION OF THE INVENTION:

These and other objects of the present invention are provided in a self examination device for the eye which is provided with an objective, convex lens mounted over a flat mirror, into which the user looks for the purpose of detecting foreign or other unwanted matter within or around the eye, or for detecting problems associated with contact lenses. A light source is provided to illuminate the eye during self examination, the path of the light source being proximate, but not through the lens and/or mirror. The device may be used in either a hand-held or portable orientation, or in the alternative, with mounting means such as legs, to enable a hands free treatment of the problems found. In order to accomplish these and other purposes, a housing defines an upwardly facing opening, into which is placed a flat, or concave upwardly reflecting mirror, upon which is mounted a convex objective lens, tailored to the needs of the circumstances, in terms of focussing as it relates to the position held or mounted and the condition of sight of the user. At some point in the housing, a chamber is provided for storage of implements required for solving the problems found by the self examination. Such chamber is provided with means to make such implements easily accessible, and yet protected during non-use. A power supply is provided within the housing, with accommodation for both adjusting the light source connected thereto in terms of focus and intensity, also adaptable to plug into a permanent power source for use particularly during the treatment period after the self examination is complete. The light source itself, either with or without fiber optics treatment capability, is arranged so that the light path from the light source flows proximate to, rather than through, the lens to the eye being examined. This provides less loss factor in the light reaching the eye and more control of the path for the light transmitted thereby.

BRIEF DESCRIPTION OF THE DRAWINGS:

Other objects, features and advantages of the present invention will become more apparent by reference to the following detailed description of the preferred and alternative, but nonetheless illustrative, embodiments of the present invention, with reference to the accompanying drawings, wherein.

Figure 1:
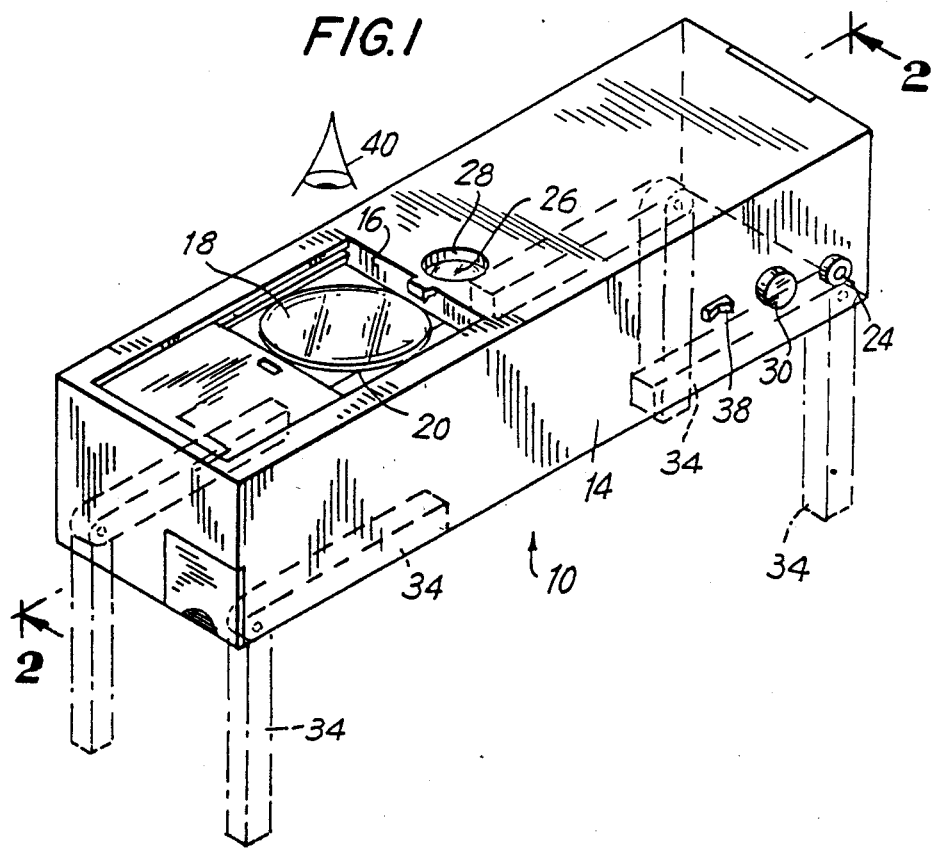
FIG. 1 is an isometric view of a device constructed according to the present invention and showing the setting in which it is typically used.
Figure 2:
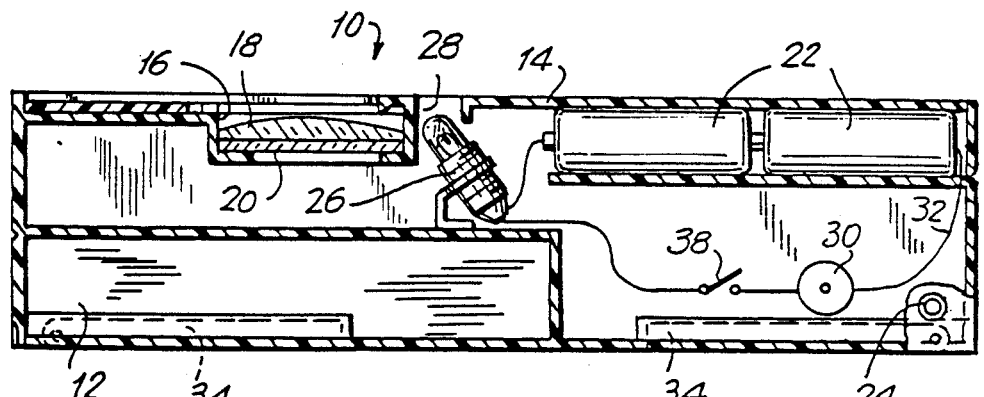
FIG. 2 is a front sectional view taken along the line 2—2 of FIG. 1 and showing particularly the placement of device elements within the device.

Referring to the drawings, a portable self examination device, generally designated 10, is shown as particularly suitable for examination of the anterior portion of the eye, the lids, and surrounding area. Device 10 is also useful for self-treatment of the eye by means of chamber 12 defined within housing 14 Housing 14 also defines an opening 16 into which is inserted an objective, convex lens 18 overlying a mirror 20. The objective lens 18 is made to particularly accommodate the visual parameters of the particular user of device 10. In other words, if the user is near-sighted, objective lens 18 is made such that the use of device 10 by such user will be as close as possible to perfect vision at the distance contemplated in order to satisfy the purpose and functions of the device.

A power source, such as batteries 22, or in the alternative, plug 24 for connection to a wall plug (not shown), is used to supply current to light source 26 in the form of a standard, but small, incandescent light source. Focussing is accomplished for the light source by, for example, and add-on lens, or use of bulbs 26 with a built-in focussing element, such as No. 222 flashlight bulb. Opening 28 defined by housing 14 enables the exposure of light source 26. Of course, rheostat 30, or the like, is provided in the light source circuit 32 in order to adjust the intensity of light source 26.

As a further feature of the present invention, storage area 12 is defined within housing 14 such that a cotton coated stick, a saline solution and medicine can be made readily available for use after the device 10 is employed to detect foreign particles or other abnormalities in the user's eye.

Alternatively, further features of the present invention are employed such as the provision of foldable legs 34 in connection with housing 14 in order to enable other than hand holding of the device during use. More importantly, legs 34, when used to mount or position device 10, allow the hands of the user to be free for the purposes of correcting a problem detected by the device. Typically, one hand is required to manipulate the eye-lids, while the other hand administers a cleaning device or medicine.

Figure 3:
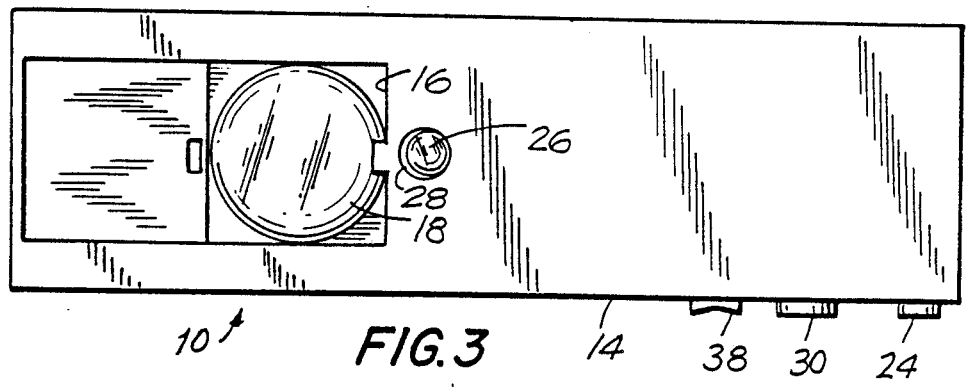
FIG. 3 is a top view of the device.
Figure 3A:
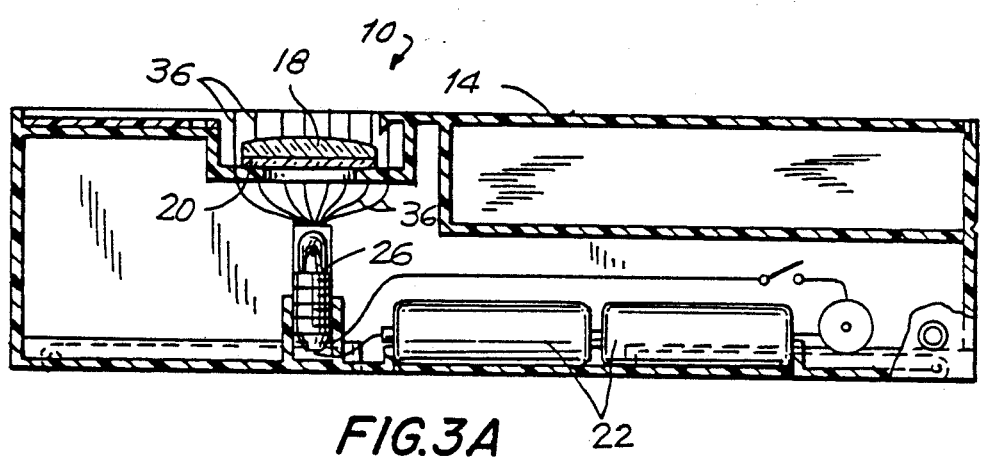
FIG. 3A is a front view similar to that of FIG. 2, but showing the use of fiber optic elements for conducting the light emanating from the light source of the device.
Figure 3B:
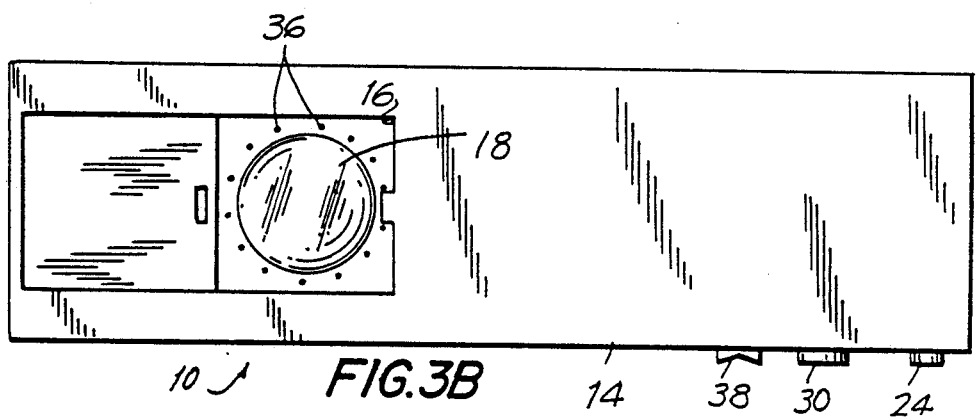
FIG. 3B is a top view of the device of FIG. 3A.

FIGS. 3A and 3B illustrate the use of fibers 36 in order to direct light from light source 26 around lens 18 and mirror 20 to the eye of the user. Thus, a direct and uniform light is employed in this alternative embodiment.

Of course, lens 18 and mirror 20 are made easily removable in order to provide for disassembly and cleaning. Likewise, light source 26 is made easily removable for replacement of its bulb. Batteries 22 are also removable and replaceable. By means well known in the art, it is also contemplated as an alternative that light source 26 be readily directable in order to enhance the use of device 10 by making the light available in order to examine the desired portion of user's eye. In practice, usually about a one-third inch square is illuminated at any one point in time; the user must therefore either move his head relative to the light/lens, or aim the light to the next area to be illuminated. This can be to another part of the surface of the eye, or to another part of the eye-lid.

In order to further enhance an understanding of all aspects of the present invention, and alternatives thereof, a typical example of use steps will now be described. Considering a typical user who is near-sighted and feels a piece of dirt in his or her eye, such user picks up device 10 with legs 34 in folded condition. Of course, lens 18, for this user's device 10, is structured to correct for near-sightedness. The user turns on the light source 26 by use of on-off switch 38 and adjusts the direction of light source 26 to accommodate his or her comfort during the examination process. The user places his or her eye 40 above lens 18 so that a reflection of the illuminated eye can be seen by the user by means of the reflection from mirror 20, in a magnified manner.

The location and severity of the dirt particle is then clearly seen and the user opens chamber 12 by means well known in the art in order to remove therefrom a cotton coated stick and a vial of saline solution for use in eliminating the dirt particle. Legs 34 are then extended in order to place device 10 upon a flat surface without being held by the user's hands. In this way, the eye can again be illuminated, and by use of the illuminated eye and the user looking through lens 18 into mirror 20, with one hand free to manipulate the lids and the other to do the cleaning, the dirt particle can be easily removed.

Of course, chamber 12 is provided with a sliding cover (not shown) or the like; and likewise, various other sliding doors and hinged covers and the like are provided throughout to make the various parts replaceable and cleanable and adjustable and removable.

The foregoing indicates clearly the elements and attributes of the present invention, which is to be limited only by the following claims:

What is claimed is:

1. An eye self-examination device for a user comprising a device housing, means for providing a light source, means for adjusting the intensity of the light source by said user, without replacement thereof, and a power supply therefor within said housing for emitting light outside of said housing, an objective lens proximate said light source, a separate reflecting device immediately beneath said objective lens for reflecting an image of an eye from without said housing, through said objective lens, the reflection of said image following a path through said objective lens.

2. An eye self-examination device for a user comprising a device housing, means for providing a light source, means for adjusting the intensity of the light source by said user, without replacement thereof, and a power supply therefor within said housing for emitting light outside of said housing, an objective lens proximate said light source, a reflecting device immediately beneath said objective lens for reflecting an image of an eye from without said housing, through said objective lens, the reflection of said image following a path through said objective lens.

3. The invention, according to claim 2, wherein means for adjusting said light source directionally are included with said device.

4. The invention, according to claim 2, wherein a storage compartment is provided within said housing.

5. The invention, according to claim 2, wherein adjustable surface mounts are provided in connection with said housing.

6. The invention, according to claim 2, wherein said light source includes fiber optic strands for emiting light in a path proximate said mirror and lens.

7. The invention, according to claim 2, wherein said objective lens is positioned upon a concave mirror, to provide a degree of magnification thereto.

8. The invention, according to claim 2, wherein said light source is a bulb having a focussing element.

9. The invention, according to claim 2, wherein said reflecting device is a flat mirror.

* * * * *